(12) United States Patent
Hermann

(10) Patent No.: US 8,964,509 B2
(45) Date of Patent: Feb. 24, 2015

(54) REMOTE COMMUNICATION AND CONTROL OF ACOUSTIC DETECTORS

(75) Inventor: Theodore Hermann, Eden Prairie, MN (US)

(73) Assignee: UTC Fire & Security Corporation, Farmington, CT (US)

( * ) Notice: Subject to any disclaimer, the term of this patent is extended or adjusted under 35 U.S.C. 154(b) by 486 days.

(21) Appl. No.: 13/332,497

(22) Filed: Dec. 21, 2011

(65) Prior Publication Data

US 2013/0163388 A1 Jun. 27, 2013

(51) Int. Cl.
*G10K 11/00* (2006.01)

(52) U.S. Cl.
USPC ............ 367/197; 367/198; 367/199; 381/110

(58) Field of Classification Search
CPC .................................. G08C 23/02; H03J 9/04
USPC ........................... 367/197–199; 381/110–117
See application file for complete search history.

(56) References Cited

U.S. PATENT DOCUMENTS

| | | | | |
|---|---|---|---|---|
| 4,575,799 A | * | 3/1986 | Miwa et al. .................... | 600/442 |
| 4,630,248 A | * | 12/1986 | Scott .............................. | 367/197 |
| 4,763,661 A | * | 8/1988 | Sommer et al. ................ | 600/443 |
| 4,790,019 A | | 12/1988 | Hueber | |
| 4,918,736 A | | 4/1990 | Bordewijk | |
| 5,012,223 A | * | 4/1991 | Griebell et al. ................ | 340/531 |
| 5,650,943 A | * | 7/1997 | Powell et al. ................... | 702/51 |
| 6,496,115 B2 | * | 12/2002 | Arakawa ..................... | 340/573.1 |
| 6,507,790 B1 | | 1/2003 | Radomski | |
| 6,760,276 B1 | | 7/2004 | Karr | |
| 8,130,595 B2 | * | 3/2012 | Ohguri et al. .................. | 367/198 |
| 2007/0115758 A1 | * | 5/2007 | Kojima et al. ................. | 367/197 |
| 2008/0310254 A1 | * | 12/2008 | Piel et al. .......................... | 367/13 |
| 2009/0040869 A1 | * | 2/2009 | Smith et al. ...................... | 367/13 |
| 2011/0142273 A1 | * | 6/2011 | Iwano et al. ................... | 381/321 |
| 2011/0193682 A1 | | 8/2011 | SeBasco | |
| 2013/0163388 A1 | * | 6/2013 | Hermann ....................... | 367/197 |
| 2013/0166227 A1 | * | 6/2013 | Hermann et al. ............... | 702/51 |

FOREIGN PATENT DOCUMENTS

| | | |
|---|---|---|
| EP | 2023305 A1 | 2/2009 |
| GB | 867764 | 12/1960 |
| GB | 412466 | 11/1975 |

OTHER PUBLICATIONS

PCT International Search Report and Written Opinion of the International Searching Authority for International Application No. PCT/US2012/070441, Apr. 17, 2013, 12 pages.

* cited by examiner

*Primary Examiner* — Brian Zimmerman
*Assistant Examiner* — An T Nguyen
(74) *Attorney, Agent, or Firm* — Cantor Colburn LLP

(57) ABSTRACT

A method of controlling a function of an acoustic detector includes storing a reference power spectrum of a reference acoustic signal, the reference power spectrum being associated with a mode of operation of the acoustic detector; receiving an acoustic sound signal, the acoustic sound signal including a tone and harmonic tones; generating a real-time acoustic power spectrum of the acoustic sound signal responsive to the receiving of the acoustic sound signal; and performing the mode of operation when a comparison of the real-time acoustic power spectrum with the reference acoustic power spectrum indicates that the acoustic sound signal is a control signal.

16 Claims, 5 Drawing Sheets

REMOTE COMMUNICATION AND CONTROL OF ACOUSTIC DETECTORS

FIELD OF INVENTION

The subject matter disclosed herein relates generally to the field of machinery condition monitoring, acoustics, and digital signal processing, and more particularly, to initiating a control function on an acoustic detector based on pattern recognition of the acoustic power spectrum generated by a unique tone or a multiplicity of tones and its harmonic components.

DESCRIPTION OF RELATED ART

Industrial operations, such as well drilling, oil production, oil refining and industrial gas production, utilize piping to move a wide variety of high-pressure fluids such as gas and liquids. The pipes move such fluids for operating and controlling industrial processes and, frequently, these gases are potentially explosive and create a hazardous condition. As such, the piping requires that it be continuously monitored for leaks. Additionally, these industrial operations utilize heavy machinery that generates sound. At these industrial plants, most man-made or machine noise occurs in the acoustic range of 20 Hz up to about 20 kHz, whereas a pressurized gas leak produces a sound signal which spans the acoustic and ultrasonic ranges. In particular, the sound signal produced by a gas leak extends into the ultrasonic frequency range above 20 kHz.

Gas leak detectors utilizing acoustic detection have been devised to measure the airborne sound pressure waves generated by the turbulent flow when a gas escapes from a high to a low pressure. These gas leak detectors are typically housed in explosion proof boxes in order to prevent ignition of any escaped gases within these hazardous locations. These hazardous locations have very limited or, in some cases, an absence of human operators. Typically, these detectors must be periodically interfaced to perform self-test, reset, or other control operations. In many installations, these detectors are deployed high on bulkheads, framework, ceiling structures, or poles. This requires maintenance and operation personnel to climb up on a ladder or scaffold to access the detector and initiate these control operations. Current devices also control these detectors using optical technology or magnetic switching with Hall Effect or similar sensors. Optical technology is limiting as it requires line of sight to the detector, while magnetic switches placed within explosion proof housings require close proximity to generate a large magnetic field in order to drive the sensor into its correct orientation. Additionally, ferrous components can divert flux thereby causing inconsistent or intermittent switching of the magnetic field. Also, RF controls have been slow to be adopted by industry due to the challenges with electromagnetic interference (EMI) as well as radiated energy in a combustible gas environment.

BRIEF SUMMARY

According to one aspect of the invention, a control system for controlling a function of an acoustic detector includes a memory that stores a reference power spectrum of a reference acoustic signal, the reference power spectrum being associated with a mode of operation of the acoustic detector; a receiver including an analog signal conditioning circuit that receives an acoustic sound signal, the acoustic signal includes a tone and harmonic tones; and a detector that performs the mode of operation when a comparison of the real-time acoustic power spectrum with the reference acoustic power spectrum indicates that the acoustic sound signal is a control signal; where the receiver generates a real-time acoustic power spectrum in response to the receiving of the acoustic sound signal.

According to another aspect of the invention, a method of controlling a function of an acoustic detector includes storing a reference power spectrum of a reference acoustic signal, the reference power spectrum being associated with a mode of operation of the acoustic detector; receiving an acoustic sound signal, the acoustic sound signal including a tone and harmonic tones; generating a real-time acoustic power spectrum of the acoustic sound signal responsive to the receiving of the acoustic sound signal; and performing the mode of operation when a comparison of the real-time acoustic power spectrum with the reference acoustic power spectrum indicates that the acoustic sound signal is a control signal.

Other aspects, features, and techniques of the invention will become more apparent from the following description taken in conjunction with the drawings.

BRIEF DESCRIPTION OF THE SEVERAL VIEWS OF THE DRAWINGS

Referring now to the drawings wherein like elements are numbered alike in the several FIGURES.

DETAILED DESCRIPTION

Embodiments of a communication and control system include an acoustic detector in acoustic communication with a remote sound source. The acoustic detector receives unique acoustic tones or signals transmitted from the remote sound source that control one or more modes of operation of the acoustic detector. The acoustic detector initiates a control function based on valid pattern recognition of the acoustic power spectrum (or sound pressure level) generated by the unique tone or a multiplicity of tones and its harmonic components. The acoustic signal includes a unique acoustic signature that is analyzed by the detector by implementing a normalized mean squared error (NMSE) function against a reference or target signature (i.e., the acoustic signature copy of the acoustic signal) stored in memory. Values of the normalized mean squared error that fall below a predetermined threshold indicate a control signal and implementation of one or more modes of operations associated with the control signal.

Figure 1:
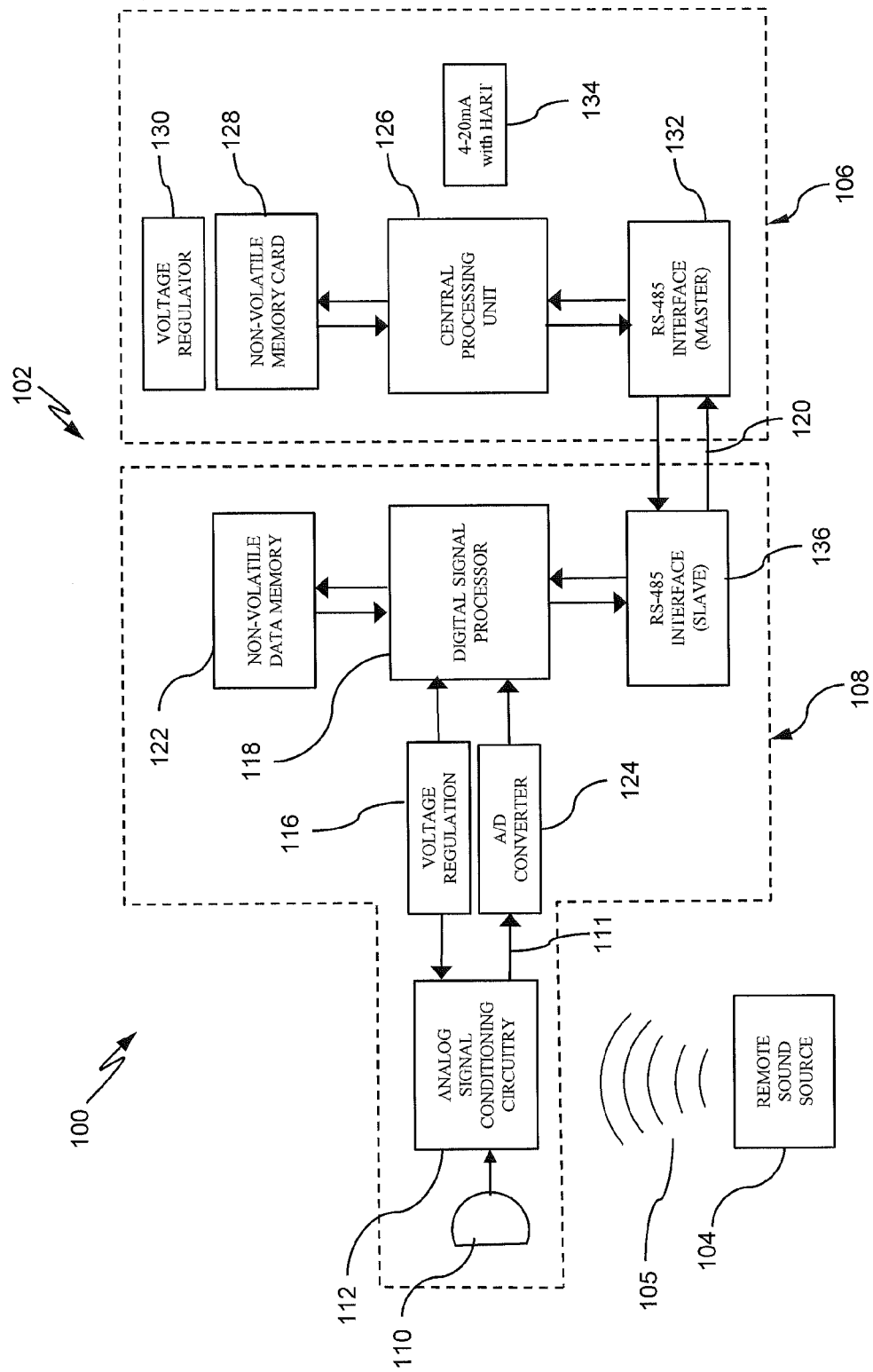
FIG. 1 illustrates a functional block diagram of the control system showing the hardware elements of the acoustic detector according to an embodiment of the invention.

Referring now to the drawings, FIG. 1 illustrates a schematic view of a communication and control system 100 including an acoustic detector 102 in acoustic communication with a remote sound source 104 according to an embodiment of the invention. Particularly, the remote sound source 104 generates acoustic signals 105 in the audible and ultrasonic frequency ranges (i.e., between 20 Hz and 80 kHz). The acoustic signals 105 initiate one or more control functions or modes of operation for the acoustic detector 102. These control functions are initiated within a hazardous location based on valid pattern recognition of an acoustic power spectrum generated by the acoustic signals 105. In one example, the remote sound source 104 includes tuned rods for emitting the acoustic signal 105 at a predetermined frequency including its harmonic components within the ultrasonic frequency range when struck and as such provides an intrinsically safe ("IS") mechanical device that does not have any electrical components that may pose a hazard for use within the hazardous location. In other embodiments, a sound source 104 such as a whistle or a piezoelectric transducer having its electrical components housed in an intrinsically safe or explosion proof housing may also be used for transmitting the unique acoustic tones or signals including its harmonic components without departing from the scope of the invention. It is to be appreciated that the sound source 104 may also be configured for providing amplitude modulated signals or frequency modulated signals for detection and control of the acoustic detector 102.

Also shown in FIG. 1, the acoustic detector 102 includes a receiver 108 in data communication 120, through a RS-485 serial communication protocol, with a control unit 106. In an embodiment, the receiver 108 includes a microphone 110 and analog signal conditioning circuitry 112, which are housed in a compact, shielded enclosure to minimize noise coupling to the acoustic input signals. In one non-limiting example, microphone 110 is of the electret condenser type and is designed to withstand severe temperature and humidity conditions, and has a high resistance to mechanical shock. Electrical design, circuit board layout, grounding, and shielding are factors in the design of microphone 110 to minimize the introduction of electrical noise into the analog signal path. The signal conditioning circuitry 112 amplifies the very low-level, single-ended voltage generated by microphone 110, passes the amplified signal through a combination of high and low pass filter circuits and a programmable gain amplifier (not shown). The high and low pass filters can be adjusted to limit incoming signals to the frequency range of interest. In this no-limiting example, the high pass filter removes frequencies below 20 Hz and the low pass filter removes frequencies above 80 kHz. A programmable gain amplifier (not shown) converts the microphone voltage to a differential voltage input 111 as input to the analog-to-digital converter 124 (A/D). Power from voltage regulation 116 supplies the microphone unit 110 with 5 volts or other suitable DC voltage. The A/D converter 124 receives the analog signal from remote microphone unit 110 and converts the differential analog signal from the signal conditioning circuitry 112 to an 18-bit digital sampled digital signal.

The speed digital signal processor 118 (DSP) continuously and in real time processes the stream of digital samples from the A/D converter 124 using a plurality of fractional octave digital bandpass filters to obtain a real-time acoustic power spectrum of the sound over a twelve octave range. In one example, the DSP 118 is a 533 MHz ADSP-BF533 DSP microcomputer manufactured by Analog Devices, Inc., however, other similar types of DSP's may be utilized without departing from the scope of the invention. When coming out of a valid reset condition, DSP 118 copies machine language instructions from non-volatile memory 122 to its on-chip program memory, and begins executing the instructions now residing in its program memory.

Also shown in FIG. 1, control unit 106 includes a DC voltage regulator 130, a central processing unit 126 (CPU), a removable non-volatile memory card 128, RS-485 transceiver 132 for data communication 120 with the receiver 108, and a 4 to 20 mA transceiver with HART protocol 134 for digital serial communications with a host system that is remotely located (not shown). The DC voltage regulator 130 is a high-efficiency linear power supply which receives electrical power from the AC mains and produces the DC voltages suitable for use by the CPU 126 and associated control unit circuitry. The CPU 126 includes a microprocessor with a computer program stored in onboard resident memory and stores the peak sound pressure level (SPL) of digitized acoustic signals at each of the 144 frequencies across 20 Hz to 80 KHz as the reference or target profile (reference acoustic signature) as well as storing real-time acoustic data. A copy of the reference profile is also saved in Non-Volatile memory card 128 such as, in one non-limiting example, a 2 GB microSD card. Additionally, the CPU 126 performs computational analysis that compares the incoming acoustic spectral content with the stored acoustic signature and implements one or more modes of operation. Further, the 4 to 20 mA transceiver with HART protocol 134 provides a 4 to 20 mA signal that is stepped to indicate, in some examples, an alarm condition (20 mA), Pre-alarm (16 mA), test (5 mA), fault (2 mA), and no fault operation (4 mA).

In operation, analog and digital signal flow through the acoustic monitor begins at the sound source 104, which transmits an acoustic signal 105 within the usable frequency range (20 Hz to 80 kHz). The acoustic signal 105 is received by microphone 110, where it is converted to a corresponding variation in voltage by microphone 110, amplified, filtered, and converted to differential form by analog signal conditioning circuitry 112, converted to digital form by analog-to-digital converter 124, and then conveyed to the serial port of DSP 118 for spectral analysis by means of a bank of digital bandpass filter frequencies. In an embodiment, there are one hundred and forty four (144) filter frequencies. The DSP 118 digitally filters the digital signals to obtain acoustic power spectrum on a logarithmic scale (decibel) or alternatively in milliWatts and transmits this digitized data to the CPU 126 using the RS-485 serial communication protocol. Also, the CPU 126 is programmed with instructions to analyze the digitized data and implement a pattern recognition algorithm for characterizing the power spectrum of the acoustic signal 105 by including its harmonics for comparison with a stored power spectrum of a reference or target profile (i.e., an acoustic signature copy of the acoustic signal 105) generated by the sound source 104 that is stored on both the onboard nonvolatile memory of the CPU 126 and the removable memory card 128. In an embodiment, the acoustic signature copy is produced in a learning mode during set-up. As a result of the comparison, the CPU 126 improves the false command rejection rate by characterizing and including the harmonic frequencies of the acoustic signal 105 in the algorithm. The CPU 126 implements the pattern recognition algorithm by normalizing the spectrum of the reference acoustic signal and the spectrum of the received acoustic signal 105 from DSP 118 and thereby accounts for the amplitude variation of the acoustic signal 105 caused by the proximity of the sound source 104 to the microphone 110.

In an embodiment, the remote sound source 104 produces a peak sound pressure level R measured at each of the detectors 144 filter frequencies. For a given frequency range of interest $f_1, \ldots, f_n$, the corresponding peak SPL at each frequency of the sound source is stored as the reference profile $R_{f_1}, \ldots, R_{f_n}$ and assigned to a detector function. Each incoming acoustic sample at the detector (i.e., a measured profile) is then compared against the reference profile $R_{f_1}, \ldots, R_{f_n}$ to determine the presence of a valid control signal condition by using a normalized mean square error (NMSE) calculation. When the calculated NMSE θ between the reference profile $R_{f_1}, \ldots, R_{f_n}$ and the real time acoustic profile over the frequency range of interest $S_{f_1}, \ldots, S_{f_n}$ is less than the user defined threshold, than the valid control signal condition is met and the assigned function can be initiated.

Assuming a relatively small spectral sensitivity across the frequency range of interest $f_1, \ldots, f_n$, the sound pressure level (SPL) increases or decreases uniformly at each frequency with the ratio 1/d to the distance d between the source 104 and detector 102. This means that a measured acoustic profile $S_{f_1}, \ldots, S_{f_n}$ will maintain a relatively constant shape as the source 104 is moved closer or further away from the detector 102, with only the amplitude or SPL varying relative to the distance d. Using the normalized MSE enables the recognition of a valid control signal independent of the distance d between the sound source and detector. The normalization adjusts both the reference profile $R_{f_1}, \ldots, R_{f_n}$ and the measured profile $S_{f_1}, \ldots, S_{f_n}$ to have a standard deviation of 1 and mean of 0. The normalized reference profile $\sim R_{f_1}, \ldots, \sim R_{f_n}$ can be determined at each frequency by the following:

$$\sim R_{f_i} = \frac{(R_{f_i} - \overline{R})}{\sigma_R}$$

where $\overline{R}$ is the average SPL of the reference profile defined as:

$$\overline{R} = \frac{1}{n}\sum_{i=1}^{n}(R_{f_i})$$

and $\sigma_R$ is the standard deviation of the reference profile defined as:

$$\sigma_R = \sqrt{\frac{1}{n}\sum_{i=1}^{n}(R_{f_i} - \overline{R})^2}$$

Similarly, the normalization of the measured profile can be determined by at each frequency from $$\theta = \frac{1}{n}\sum_{i=1}^{n}(\sim S_{f_i} - \sim R_{f_i})^2$$

The mean square error θ for the normalized reference and measured profiles is determined by the following:

$$\sim S_{f_i} = \frac{(s_{f_i} - \overline{s})}{\sigma_S}.$$

It should be noted that this communication approach is independent of time duration, that is, a single acoustic sample can instantaneously initiate action. Alternatively, the communication algorithm can be implemented to ensure that the valid control signal condition exists for a specified time duration, or number of acoustic samples by the detector.

In some non-limiting examples, a 40 kHz signal may be utilized to initiate a self-test, a 50 kHz signal for a detector reset, or the like. In other examples, the control source 104 may be utilized to prove amplitude modulated signals for controlling the acoustic detector 102. For example, a 40 kHz signal modulated at 5 Hz could initiate self test, while a 40 kHz signal modulated at 12 Hz could initiate a detector reset. In other embodiments, the sound source 104 may be configured for providing frequency modulated signals for detection and control of the frequency detector 102 such as, for example, frequency modulation between 6 kHz and 40 kHZ may control self-test while modulation between 35 kHz and 40 kHz may control detector reset.

Figure 2:
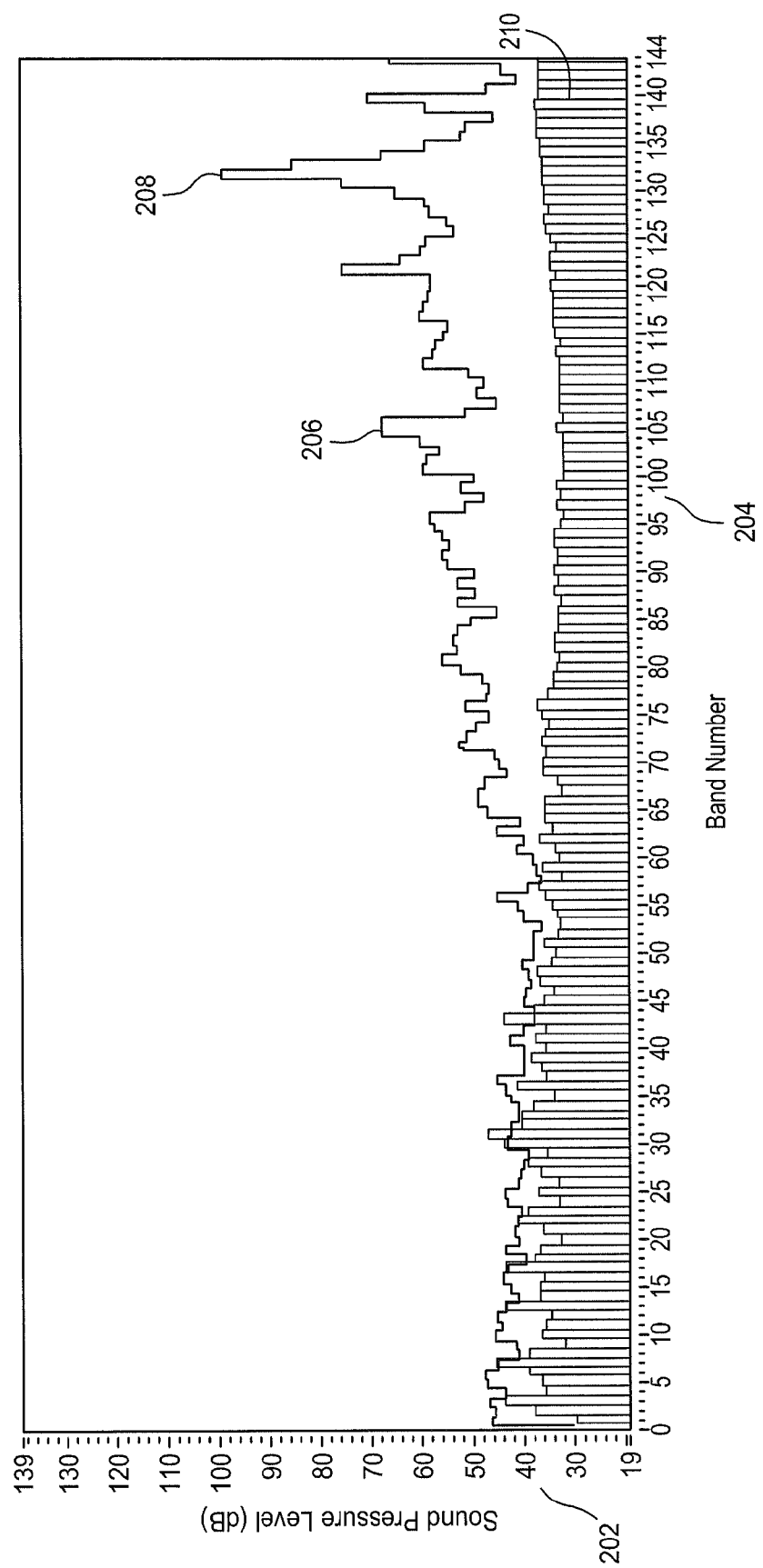
FIG. 2 illustrates a graph showing an acoustic signature and the reference signature according to an embodiment of the invention.
Figure 3:
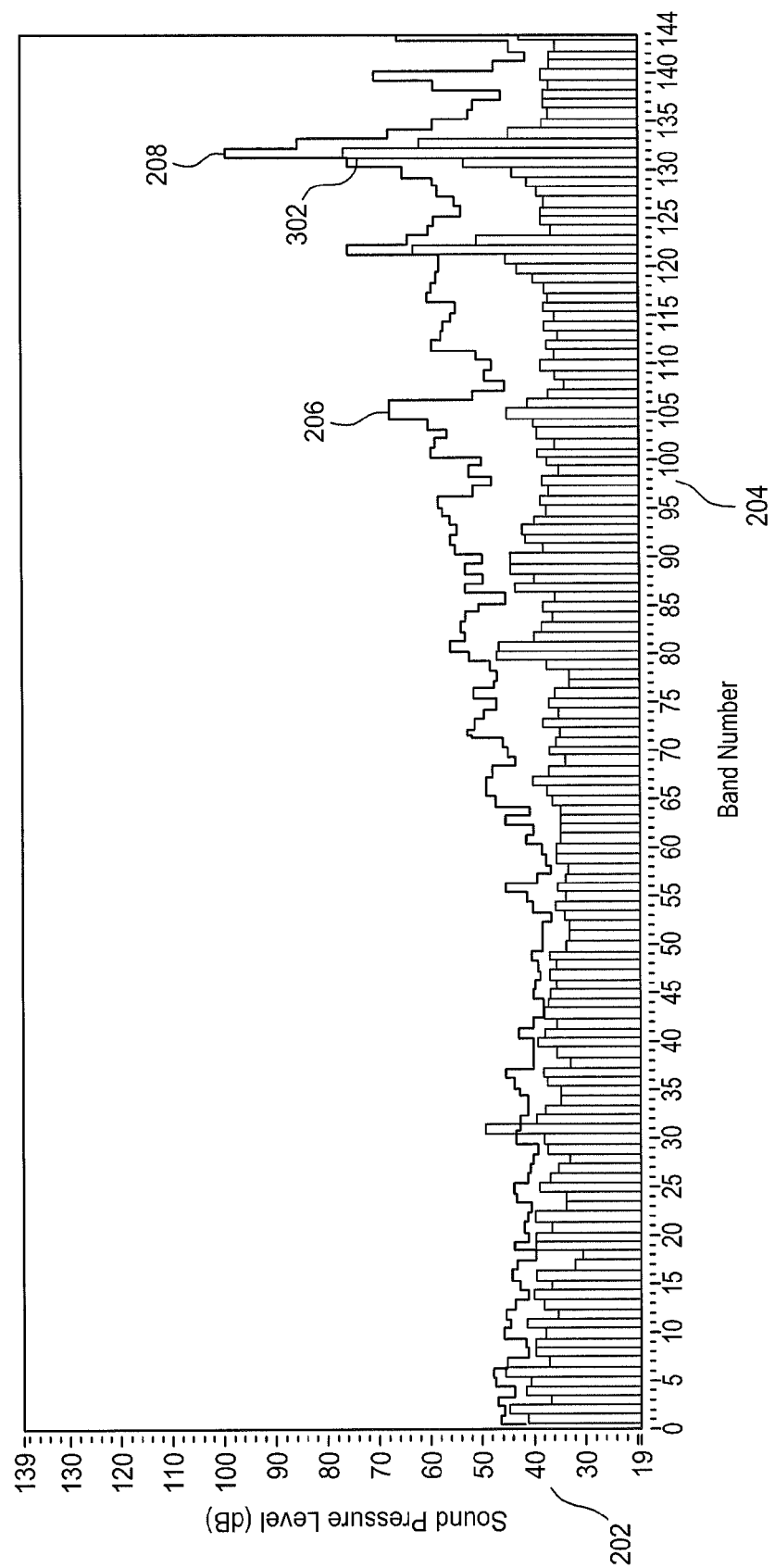
FIG. 3 illustrates a graph showing a spectrum of an acoustic signature generated from a source away to the detector according to an embodiment of the invention.
Figure 4:
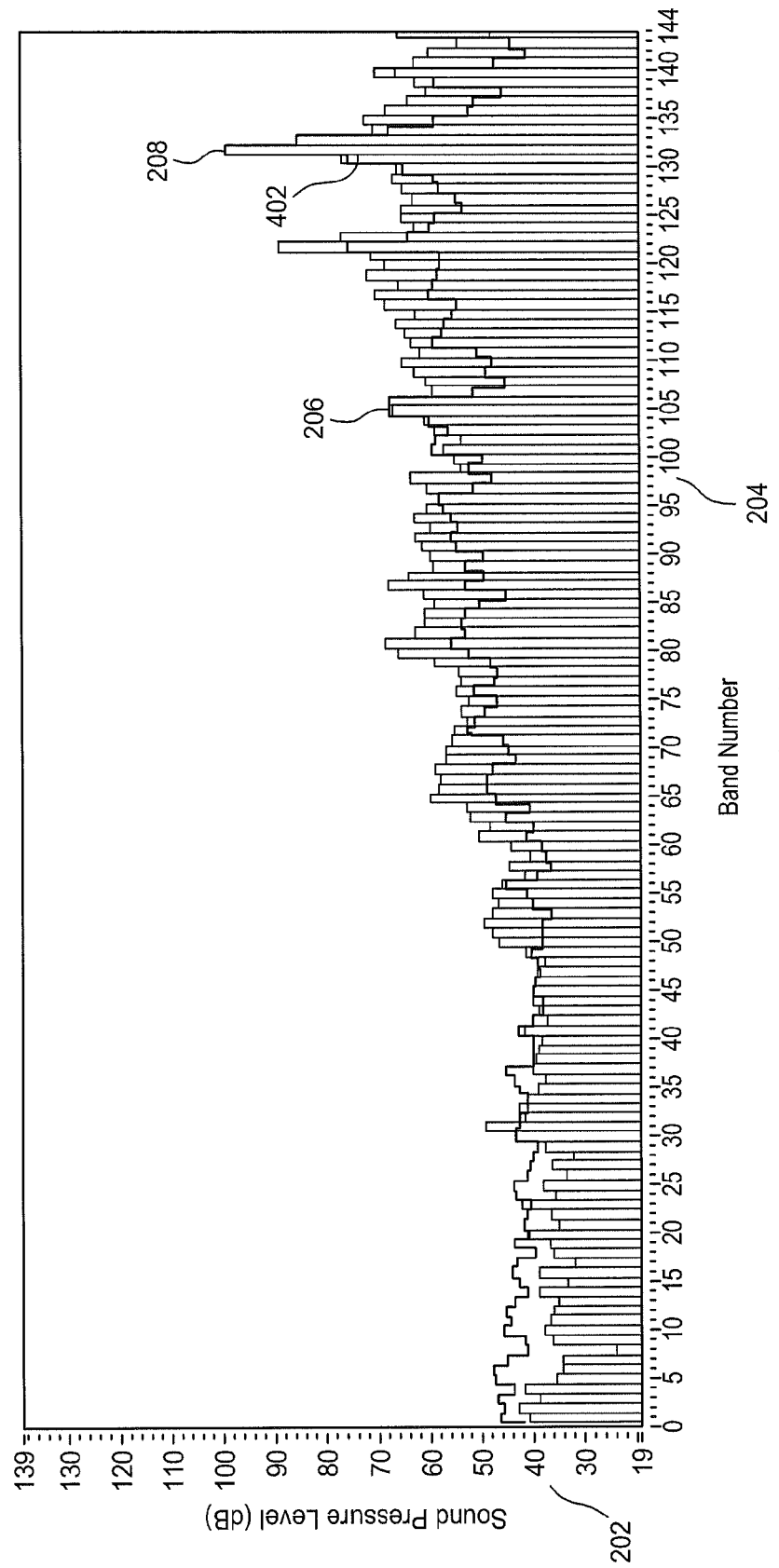
FIG. 4 illustrates a graph showing a spectrum of an acoustic signature generated from a source close to the detector according to an embodiment of the invention.

FIGS. 2-4 depict an exemplary acoustic spectrum from 20 Hz to 80 kHz for various acoustic signals that are analyzed by the detector 102 (FIG. 1) by implementing a normalized mean squared error (NMSE) function against a reference or target signature or profile according to an embodiment of the invention. The acoustic detector 102 (FIG. 1) can look across a wide frequency range and command signals may occupy all or part of the useable spectrum. In the example shown in FIGS. 2-4, the filter bands 60 through 144 are used as the range to identify potential matches to a learned baseline 206 that includes a reference profile. The remote sound source produces a peak sound pressure level measured at each of the detectors filter frequencies across frequency range of interest. The peak SPL at each frequency in this range is stored as the reference or target profile and assigned to a detector function. Each incoming acoustic sample at the detector 102 (FIG. 1) is then compared against the reference profile to determine the presence of a valid control signal condition by using a normalized mean square error (NMSE) calculation. The normalization adjusts both the reference profile and the measured profile to have a standard deviation of 1 and mean of 0. Assuming a relatively small spectral sensitivity across the frequency range of interest, the sound pressure level should increase or decrease relatively uniformly at each frequency. This means that a measured acoustic profile will maintain a relatively constant shape as the source is moved closer or further away from the detector 102, with only the amplitude or SPL varying relative to the distance. Using the normalized MSE enables the recognition of a valid control signal independent of the distance between the sound source and detector.

As shown in FIGS. 2-4, the vertical scale 202 is the sound pressure level in decibels while the horizontal scale 204 are the frequency bands as a result of filtering the ¹⁄₁₂th octave bands over a twelfth octave range for 144 bands or divisions. The received acoustic signal includes a unique acoustic signature that is analyzed by the detector by implementing a normalized mean squared error (NMSE) function against a reference signature i.e., the acoustic signature copy of the acoustic signal) stored in memory. At a predetermined and adjustable level of the NMSE threshold, this level being set at 0.5 for the example shown in FIGS. 2-5, values of the NMSE that fall below a predetermined threshold indicate a control signal and implementation of one or more modes of operations associated with the control signal. The reference profile 206 represents reference stored peak values for the impulse response of striking a reference source, which is a tuned aluminum rod. In the example shown, there is a main lobe 208 at band 132, pronounced harmonic side lobes at lower SPLs (at bands 120, 139, and 144), as well as some audible noise in the range between band 60 and band 100. Particularly, in FIG. 2, each of the 144 frequency bands from 20 Hz to 80 KHz is represented by spectrum 210 corresponding to the sound pressure level (SPL) across the 144 bands. It is to be appreciated that the greater the uniqueness of signal characteristics such as, for example, center frequency, ratio of harmonic nodes, etc., the greater the ability to discern the SPL of the remote sound source 104 from spurious noise and reject false command signals. It is to be appreciated that although a 1/12th octave filtering is being shown here, the spectral content could also be generated by the FFT method.

Shown in FIG. 3 is the acoustic spectrum 302 for an acoustic signal from a sound source 104 (FIG. 1) that is positioned several meters away from the detector and the resulting SPL for acoustic signal is low with respect to the reference profile 206. Despite the lower SPL of the command signal 302, it is recognized by the detector 102 since the shape of the waveform is close enough to the reference profile to fall below the NMSE threshold of 0.5 in this example, and the detector 102 will initiate a function associated with the acoustic signal 302.

Shown in FIG. 4 is the acoustic spectrum 402 for an acoustic signal from a sound source 104 (FIG. 1) that is positioned very close to the detector 102 and the resulting SPL for an acoustic signal that results in a higher amplitude or SPL with respect to the reference profile 206. Again the measured NMSE falls below the defined threshold of 0.5 and will be recognized as a control signal and the detector 102 will initiate a function associated with the acoustic signal.

Figure 5:
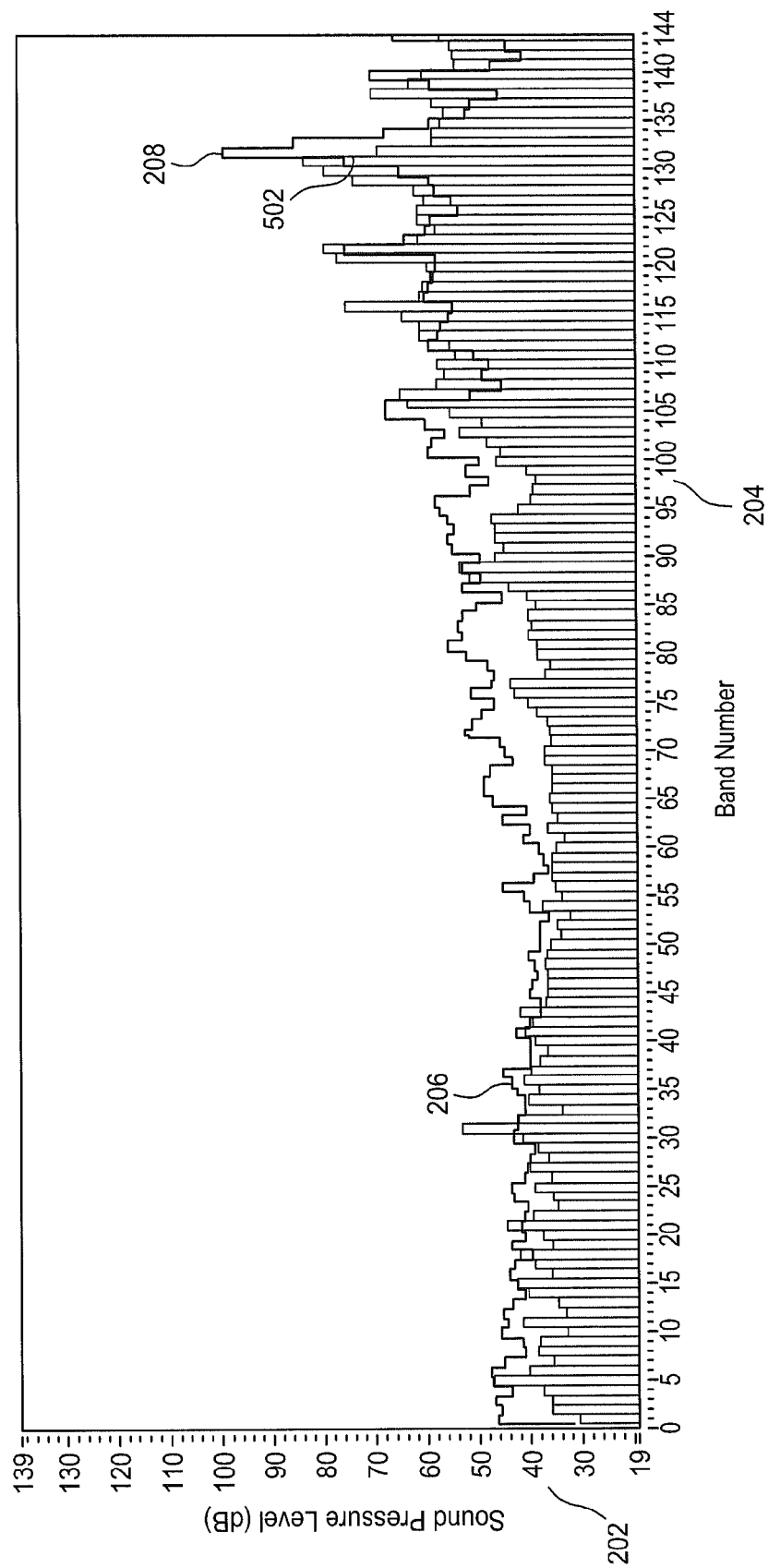
FIG. 5 illustrates a graph showing a spectrum of an acoustic signature generated from a noise sources according to an embodiment of the invention.

Shown in FIG. 5 is the acoustic spectrum 502 for an acoustic signal from several spurious noise sources. The acoustic waveform 502 results in a very close wave form to the reference profile 206, however the best spurious reproduction that was able to be generated resulted in an NMSE of approximately 0.8, which is above the exemplary threshold of 0.5. As such, the detector 102 will not initiate any function with the acoustic signal. The technical effects and benefits of exemplary embodiments include a communication and control system having an acoustic detector in acoustic communication with a remote sound source. The acoustic detector receives unique acoustic tones or signals transmitted from the remote sound source that control one or more modes of operation of the acoustic detector. The acoustic detector initiates a control function based on valid pattern recognition of the acoustic power spectrum (or sound pressure level) generated by the unique tone or a multiplicity of tones and its harmonic components.

The terminology used herein is for the purpose of describing particular embodiments only and is not intended to be limiting of the invention. While the description of the present invention has been presented for purposes of illustration and description, it is not intended to be exhaustive or limited to the invention in the form disclosed. Many modifications, variations, alterations, substitutions, or equivalent arrangement not hereto described will be apparent to those of ordinary skill in the art without departing from the scope and spirit of the invention. Additionally, while the various embodiment of the invention have been described, it is to be understood that aspects of the invention may include only some of the described embodiments. Accordingly, the invention is not to be seen as limited by the foregoing description, but is only limited by the scope of the appended claims.

The invention claimed is:

1. A control system for controlling a function of an acoustic detector, comprising:
   a memory that stores a reference power spectrum of a reference acoustic signal, the reference power spectrum being associated with a mode of operation of the acoustic detector;
   a receiver including an analog signal conditioning circuit that receives an acoustic sound signal, the acoustic signal includes a tone and harmonic tones, wherein the receiver generates a real-time acoustic power spectrum in response to the receiving of the acoustic sound signal; and
   a detector that performs the mode of operation when a comparison of the real-time acoustic power spectrum with the reference power spectrum indicates that the acoustic sound signal is a control signal;
   wherein comparing the real-time acoustic power spectrum with the reference power spectrum includes normalizing each of the real-time acoustic power spectrum and the reference power spectrum and calculating a normalized mean squared error between the normalized real-time acoustic power spectrum and the normalized reference power spectrum and comparing the normalized mean squared error to a threshold to indicate that the acoustic sound signal is the control signal.

2. The control system of claim 1, wherein the receiver comprises a microphone that generates an analog electrical signal representative of the acoustic sound signal within an audible frequency range over a plurality of octaves.

3. The control system of claim 2, wherein the receiver comprises an analog-to-digital converter that samples the analog signal at regular intervals and converts it to a stream of digital samples.

4. The control system of claim 3, wherein the receiver comprises a digital filter coupled to the analog-to-digital converter that processes the stream of digital samples from the analog-to-digital converter continuously and in real time using a plurality of fractional octave digital bandpass filters to obtain the real-time acoustic power spectrum of the acoustic sound signal.

5. The control system of claim 1, wherein a source of the acoustic sound signal is one of a tuned rod, a whistle, or a piezoelectric transducer.

6. The control system of claim 1, wherein the detector comprises a processor that analyzes a spectrum of the real-time acoustic power spectrum.

7. The control system of claim 1, wherein the detector performs the one or more modes of operation when the normalized mean squared error is below the threshold.

8. The control system of claim 1, wherein the acoustic sound signal is one of an unmodulated acoustic signal, a frequency modulated acoustic signal, or an amplitude modulated acoustic signal.

9. A method of controlling a function of an acoustic detector, comprising:
   storing a reference power spectrum of a reference acoustic signal, the reference power spectrum being associated with a mode of operation of the acoustic detector;
   receiving an acoustic sound signal, the acoustic sound signal including a tone and harmonic tones;
   generating a real-time acoustic power spectrum of the acoustic sound signal responsive to the receiving of the acoustic sound signal; and
   performing the mode of operation when a comparison of the real-time acoustic power spectrum with the reference power spectrum indicates that the acoustic sound signal is a control signal;
   wherein comparing the real-time acoustic power spectrum with the reference power spectrum includes normalizing each of the real-time acoustic power spectrum and the reference power spectrum and calculating a normalized mean squared error between the normalized real-time acoustic power spectrum and the normalized reference power spectrum and comparing the normalized mean squared error to a threshold to indicate that the acoustic sound signal is the control signal.

10. The method of claim 9, further comprising generating an analog electrical signal representative of the acoustic sound signal responsive to the receiving of the acoustic sound signal, the analog electrical signal representing an audible frequency range over a plurality of octaves.

11. The method of claim 10, further comprising sampling the analog signal at regular intervals and converting it to a stream of digital samples.

12. The method of claim 11, further comprising processing the stream of digital samples from the analog-to-digital converter continuously and in real time using a plurality of fractional octave digital bandpass filters to obtain the real-time acoustic power spectrum of the acoustic sound signal.

13. The method of claim 9, wherein a source of the acoustic sound signal is one of a tuned rod, a whistle, or a piezoelectric transducer.

14. The method of claim 9, wherein the detector comprises a processor configured for spectral analysis of the real-time acoustic power spectrum.

15. The method of claim 9, further comprising performing the mode of operation when the normalized mean squared error is below the threshold.

16. The method of claim 9, wherein the acoustic sound signal is one of an unmodulated acoustic signal, a frequency modulated acoustic signal, or an amplitude modulated acoustic signal.

* * * * *